United States Patent [19]

Kovacs et al.

[11] 3,992,556

[45] Nov. 16, 1976

[54] SUPPLEMENTED FOOD PRODUCT

[75] Inventors: Louis E. Kovacs, Chicago, Ill.; Richard Merriam Vondell, Battle Creek, Mich.

[73] Assignee: Vitamins, Inc., Chicago, Ill.

[22] Filed: June 30, 1975

[21] Appl. No.: 591,707

Related U.S. Application Data

[63] Continuation-in-part of Ser. No. 358,019, May 7, 1973, abandoned, which is a continuation-in-part of Ser. No. 40,384, May 15, 1970, abandoned.

[52] U.S. Cl. ................................. 426/72; 426/74; 426/89; 426/96; 426/97; 426/99; 426/290; 426/311; 426/619; 426/620; 426/621
[51] Int. Cl.² ......................................................... A23L 1/30
[58] Field of Search .................. 426/72, 73, 74, 89, 426/93, 97, 96, 98, 99, 289, 290, 291, 311, 615, 621, 620, 549, 619

[56] References Cited

UNITED STATES PATENTS

| | | | |
|---|---|---|---|
| 2,685,517 | 8/1954 | Dunmire | 426/72 |
| 2,777,797 | 1/1957 | Hochberg et al. | 424/14 |
| 2,937,091 | 5/1970 | Rosenberg | 426/73 X |
| 3,035,985 | 5/1962 | Stoyle | 424/147 X |
| 3,458,623 | 7/1969 | Raymond | 424/38 |
| 3,784,716 | 1/1974 | Spangler | 426/289 |

FOREIGN PATENTS OR APPLICATIONS 780,022    1957    United Kingdom

OTHER PUBLICATIONS

Matz, "The Chemistry and Technology of Cereals as Food and Feed", Avi Publishing Co. Inc., 1959, pp. 553–554.

*Primary Examiner*—Raymond N. Jones
*Attorney, Agent, or Firm*—Merriam, Marshall, Shapiro & Klose

[57] ABSTRACT

Food products are supplemented with food supplements comprising finely divided particles of edible, metabolizable fat carrier having mixed therein a nutrient selected from the group consisting of assimilable iron compound, vitamins, minerals and mixtures thereof. Preferably the food supplement is affixed to the food product by applying the supplement to the surface of the food product while said surface is at a temperature above the melting point of the fat carrier.

15 Claims, No Drawings

SUPPLEMENTED FOOD PRODUCT

This application is a continuation-in-part of copending application Ser. No. 358,019 filed May 7, 1973, now abandoned, which in turn is a continuation-in-part of application Ser. No. 40,384 filed May 15, 1970, now abandoned.

The present invention is generaly directed to food products in which a food supplement has been incorporated and the means for incorporating the food supplements. More particularly, the present invention is directed to a particulate food supplement composition comprising a nutrient such as assimilable iron compounds, vitamins, minerals or mixtures thereof which nutrient is uniformly dispersed in a carrier consisting essentially of particles or beads of an edible metabolizable fat. The edible fat is solid at room temperature, with a preferred softening or melting point between about 100° and 250° F., whereby said assimilable iron compounds, vitamins, minerals or mixtures thereof can be conveniently added or applied to a variety of foods, such as breakfast food cereals, crackers, cookies, potato chips and similar snack foods, flour and pasta during their productions.

Although this invention is broadly directed to food supplements containing assimilable iron compounds, vitamins, minerals or mixtures thereof, and to the addition of such supplements to various base food products, for simplicity, the following discussion will be principally directed to supplements containing assimilable iron compounds and the addition of assimilable iron compounds to food products.

The need for iron in the diet of humans in order to avoid or cure iron deficiency and the symptoms associated therewith has been well documented.

The Director of the National Clearing House for Nutrition and Health for the U.S. Department of Health, Education and Welfare recently reported on a nutritional survey taken over a 2-½ year period. The survey showed that a surprising number of people in this country had low or unacceptable hemoglobin levels. The survey showed that in the adolescent group, 10 to 15% in some states and as high as 40% in others, showed low hemoglobin levels and the problem was seemingly unrelated to any income or ethnic group. The survey also showed a high incidence of low hemoglobin level in people over 60 years of age, and among pre-school children at a nation-wide rate of close to 20%. The Director reported that the majority of these problems can be traced back to a lack of iron. The wide-spread nutritional anemia to the United States is well documented and recognized. The need for increased iron intake as part of the daily diet is imperative. A product and method for accomplishing this practice is the subject of this invention.

While the need for dietary iron has been long recognized, the prior art was handicapped by the fact that many iron compounds tend to cause off-flavors in food stuffs and/or tend to promote rancidity. In fact some of the best iron compounds, from the biological availability point of view, are the worst offenders in causing rancidity and the like. For instance, recent studies on the addition of offerrous sulfate and ferric ammonium citrate to flour showed that the mixtures containing ferrous sulfate became rancid shortly after preparation and the mixtures containing ferric ammonium citrate became rancid after a short storage. It is known that ferrous sulfate, or other soluble iron sources, when combined with rice or corn and common flavoring components such as sucrose, salt, etc., will discolor the entire mass when it is subjected to moist heat, such as is encountered in a cooking process. It is also known that ferrous sulfate topically applied to rice or corn cereals, as an aqueous spray, causes a metallic off-taste and shortened shelf life. Although small quantities of less soluble iron compounds, which typically have a low biological availability, may be used in food without causing such problems, it is when the quantities of such iron compounds are increased to significant levels, i.e., above 10% of the RDA, that problems are encountered. It is also well known that some vitamins and/or minerals (in addition to iron compounds) also cause off-flavors or tend to promote rancidity in foods.

In its preferred embodiment, the present invention provides a bead-like form of iron compounds, vitamins, minerals, or mixtures thereof which may be conveniently added to foods in significant quantities, which does not impair the shelf life of the foods, and which does not impart undesired taste or color to the food. Thus, a product can be produced which has the foregoing attributes and which contains a large quantity of iron having a high biological availability index. The present invention provides an efficient means by which foods can be nutritionally supplemented or fortified without creating problems affecting flavor, odor, color, stability, compatabilities and bioavailability.

It has been found that by dispersing the iron or the iron compounds in a solid fat carrier, none of the iron taste or the iron compound taste is imparted to the food directly and there is avoidance of discoloration, of off-flavors and off-odors of the iron fortified foods. Many vitamins and minerals, particularly when used in combinations, are unstable and have undesirable odor, color, or flavor and/or tend to promote rancidity in food. Further some vitamins deteriorate unless protected against oxidation or the presence of minerals or other vitamins. Such problems are also avoided by coating these materials with an assimilable fat in accordance with the present invention. After the fortified foods are consumed and the iron compounds, vitamins, and/or minerals supplement passes into the stomach, the edible fat is manipulated to release the iron compounds, vitamins, and/or minerals and these materials are available to be absorbed into the body. Thus the fat coating tends to protect the iron compounds, the vitamins and the minerals until they pass into the stomach.

The present invention provides assimilable iron compounds, vitamins, minerals or mixtures thereof in a form which is easily and palatably used with various foods. By coating assimilable iron compounds, vitamins, minerals or mixtures thereof with a fat carrier to form the food supplement, the edible solid fat protects the foods on which it is used from discoloration, odor and flavors caused by the iron compounds, vitamins, minerals or mixtures thereof, and shields the eater of the foods from tastes thereof, and some digestive discomforts. Breakfast cereals, crackers, cookies, potato chips and similar snack foods are subjected to cooking, drying and/or toasting process during their manufacture. Following the toasting process, and while the food is still hot, it is possible to simply sprinkle the beads of the food supplement of the present invention on the hot base foods, whereby the fat will be softened by heat from the base foods, and the particles of the food supplement will adhere to the food product, using the fat carrier as an adhesive. This invention thus provides a convenient form for supplementing the iron, the vitamin or the mineral content of such foods.

The iron compound which is used in the present invention must contain iron in a form which is available to the body at the site of absorption. It is preferred that the iron compound be a finely divided solid, and it is essential that the iron compound be compatible with the fat used.

While the present invention is not limited to any particular iron-containing compound, dried ferrous sulfate U.S.P., described in the examples, is a preferred form of iron for use in the present invention because of its proven usefulness as an oral iron medicament, its economy, and because of its biological availability.

Listed below are a number of iron-containing compounds which may be used to produce the assimilable iron compositions of the present invention. Listed along side of the compound is a number, under the caption "Average Relative Biological Value" which is a value reported in the prior art relating to the biological assimilability of the compound, using ferrous sulfate as 100. These compounds are:

| COMPOUND | AVERAGE RELATIVE BIOLOGICAL VALUE |
|---|---|
| ferric ammonium citrate | 107 |
| ferric choline citrate | 102 |
| ferrous sulfate | 100 |
| ferrous ammonium sulfate | 99 |
| EDTA, dihydrogen ferrous salt | 99 |
| ferrous chloride | 98 |
| ferrous gluconate | 97 |
| ferrous fumarate | 95 |
| ferric glycerophosphate | 93 |
| ferric sulfate | 83 |
| ferrous tartrate | 77 |
| ferric citrate | 73 |
| ferric pyrophosphate | 45 |
| ferric chloride | 44 |
| reduced iron | 37 |
| ferric orthophosphate | 14 |
| sodium iron pyrophosphate | 14 |
| ferric oxide | 4 |
| ferrous carbonate | 2 |

Although any of the compounds listed above as well as many other iron-containing compounds may be used, it is preferred to use compounds which contain high average relative biological value. The present invention likewise contemplates the use of mixtures of iron-containing compounds. While the examples presented below show the use of ferrous sulfate which passes 100 mesh, finer or coarser sizes may be used. For instance, iron-containing compounds of 20 mesh or as fine as 325 mesh can be used in the present invention. It is essential that the iron-containing compound be a particulate solid material which is substantially finer in size than the size of the final bead-like product. The bead-like product size may vary over a wide range and may conveniently be from about 10 to 300 mesh.

The present invention contemplates the production of food supplements containing vitamins or minerals, as well as the iron compounds. The iron compounds, the vitamins, and the minerals may be combined in any desired proportion or combination, provided the mixtures are compatible, and admixed with the metabolizable fat or these materials may be processed separately and either used separately or combined for use. The following vitamins and minerals are considered to be essential in human nutrition and the FDA has established the quantities given below as the Recommended Daily Allowances (RDA) of thse nutrients (see Department of Health, Education and Welfare, Food and Drug Administration in "Regulations for Nutrition Labeling," Federal Register, Vol. 38, No. 49, March 14, 1973). Any of the below listed nutrients may be used individually or in combination in the food supplements of the present invention:

| NUTRIENT | RDA |
|---|---|
| Vitamin A | 5000 IU |
| Vitamin C (ascorbic acid) | 60 mg |
| Vitamin $B_1$ (thiamine) | 1.5 mg |
| Vitamin $B_2$ (riboflavin) | 1.7 mg |
| Niacin | 20 mg |
| Calcium | 1.0 gram |
| Iron | 18 mg |
| Vitamin D | 400 IU |
| Vitamin E | 30 IU |
| Vitamin $B_6$ | 2.0 mg |
| Folic acid | 0.4 mg |
| Vitamin $B_{12}$ | 6 $\mu$ |
| Phosphorus | 1.0 gram |
| Iodine | 150 $\mu$ |
| Magnesium | 400 mg |
| Zinc | 15 mg |
| Copper | 2 mg |
| Biotin | 0.3 mg |
| Pantothenic acid | 10 mg |

IU—International Units
$\mu$—micrograms
mg—milligrams

The FDA has also established 10% of the RDA as the lowest level at which a nutrient is meaningful or sigificant. Under Section (b) (7) (v), the Regulation on Nutritional Labeling states that:

"No claim may be made that a food is a significant source of a nutrient unless that nutrient is present in the food at a level equal to or in excess of 10 percent of the U.S. RDA in a serving (portion)."

Ten percent (10%) of the RDA for iron would be 1.8 mg. Other materials which are thought to affect human nutrition, other than the vitamins and minerals considered to be essential, may be similarly made up into food supplements using the teachings of the present invention if desired. Such other materials include:

Cobalt
Manganese
Molybdenum
Menadione
Phytonadione.

In preparing mixtures of iron compounds and/or vitamins and/or minerals it is essential to avoid the production of incompatible mixtures. Although it is somewhat more expensive to separately coat all materials, no nutritional problems are occasioned by separately coating elements which are actually compatible. For instance, it has been found that Vitamin A and Vitamin D can be mixed together and then coated with fat to provide a stable food supplement. It is also possible to separately coat the Vitamin A and Vitamin D. Separate coating provides a convenient means by which the relative proportion of Vitamin A and Vitamin D may be used in various food supplements.

On the other hand, there are certain combinations or mixtures which create odor, flavor or stability problems. It has been observed that Vitamins C, $B_1$, and $B_{12}$ have certain flavor and odor incompatabilities, with and without degradation of the potencies. Vitamins C and $B_{12}$ do not appear to be as bad in flavor and odor as Vitamins $B_1$ and $B_{12}$ or Vitamins $B_1$ and C. Vitamin $B_1$ has been found to be particularly bad when combined with any of them. It is also known that some forms of Vitamin E tend to oxidize readily in the presence of iron salts, therefore Vitamin E should be coated separately from the iron compounds. Ascorbic acid is known to oxidize in the presence of copper and iron. Therefore, care should be taken to keep copper and iron separate from the Vitamin C mixtures. Thiamine hydrochloride is unstable in the presence of iodine and should be segregated therefrom. Vitamin $B_{12}$ deteriorates in the presence of ascorbic acid, and ferrous sulfate and should be separated therefrom. Additionally, many of the vitamins are sensitive to pH or light or heat. It has been found that when the vitamins are separately coated, in accordance with the present invention, incompatibilities attributable to pH can be substantially eliminated, and sensitivity to light and heat can be reduced.

The present invention further contemplates the preparation of food supplements containing vitamins and minerals mixed with the assimilable iron compounds. In the case of vitamins and minerals which are compatible or stable with each other and do not deteriorate in the presence of iron compounds, such as Vitamin $B_1$ or copper, the vitamins and minerals can simply be mixed with the iron compound and melted fat to form a homogeneous slurry which is then subdivided and cooled.

However, for those vitamins and/or minerals which are not compatible with each other or are reactive with or deteriorate in the presence of iron, such as Vitamin A, care must be taken to avoid the deterioration. Such vitamins and/or minerals may be separately mixed with melted fat, in the absence of compounds or other incompatible materials, to form a homogeneous slurry which may be subdivided and cooled. The particles thereby produced may be mixed with beads of fat containing iron compounds. Thus the present invention provides a means to produce a food supplement containing mixtures of vitamins and/or minerals, either with or without an iron supplement in any desired proportions and in a physical form which is conveniently handled and easily applied to foods. Alternatively, vitamins and/or minerals may be individually dispersed in fats using the techniques described herein and used as individual components, separate from each other and separate from the iron supplement.

The fat used to encapsulate or coat the iron compounds, vitamins, and/or minerals for use in the present invention must be an edible metabolizable fat, which is solid at room temperature, and preferably has a melting point of at least 100° F., but not more than about 250° F. It is preferred that the fat be essentially free from taste producing components. Among the types of fat which may be used are the distilled monoglycerides, from hydrogenated vegetable or animal oils, and various other vegetable or animal fats which can be metabolized in order that the iron compound be freed for absorption. The present invention contemplates the use of hydrogenated cottonseed oil, coconut oil, palm kernel oil, hydrogenated peanut oil, hydrogenated soy bean oil, hydrogenated lard and other edible materials melting between about 100° and 250° F. Preferably these oils or fats are refined to remove flavor conferring bodies before they are used. Good results have been obtained using commercially available distilled monoglycerides made from fully hydrogenated cottonseed oil having the formula

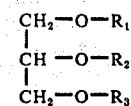

where $R_1$ is an acyl radical derived from saturated and unsaturated aliphatic acids having between 14 and 18 carbon atoms per molecule and $R_2$ and $R_3$ are primarily hydrogen or not more than 10% $R_1$. Such a material is sold under the trade name MYVEROL 18-07. The present invention also contemplates the use of commercially available straight hydrogenated cottonseed oil having a melting point of 140°–145° F., since it is more economical.

The method by which iron compounds, vitamins, minerals or mixtures thereof are encapsulated by the fat or oil may be varied over wide limits. For purposes of the present invention it is not necessary that the fat carrier uniformly coat the food supplement component with a monolithic film. The present invention contemplates the components to be enrobed or enveloped in the fat carrier which may take the form of a relatively large irregular particle. The examples set forth below illustrate the preferred method wherein the fat is heated until it becomes liquid and iron compounds, vitamins, minerals or mixtures thereof are added thereto to form a uniform slurry or suspension. The slurry is then subdivided into droplets or bead-like particles and, while in subdivided form, it is cooled. The slurry may be conveniently subdivided by spraying, but other methods may also be used. Various commercial equipment may be used for atomizing the slurry such as spray dryers of tower or box type equipped with high pressure nozzles.

Alternatively, the slurry of iron compounds, vitamins, minerals or mixtures thereof and liquid fat may be first cooled to produce a solid and then the solid may be subdivided. The present invention contemplates cooling using cryogenic methods followed by low temperature grinding in order to produce very finely divided products, such as beads which pass a 150 mesh.

The following examples serve to illustrate the preparation of several food supplements within the present invention, but it is understood that the examples are set forth for merely illustrative purposes and that many other food supplements are within the scope of the present invention.

EXAMPLE 1

An assimilable iron supplement which contained approximately 27.6% by weight of dried ferrous sulfate was made as follows: A distilled monoglyceride oil made from hydrogenated cottonseed oil, having a melting point of 164° F. (about 250 pounds) was heated in an open stainless steel 50 gallon tank by a gas burner underneath. The melting took about 1 hour. In the meantime, steam was used to heat all other lines, pumps and tanks. When the oil reached a temperature of about 200° F., it was pumped into a preheated 500 gallon tank and circulated continuously. Additional oil was addded to the large tank keeping the temperature of the mix above 180° F. until a total of 2000 pounds of oil had been melted. It took 1.5 hours to melt the balance of 1750 pounds of oil. Then 762 pounds of dried ferrous sulfate U.S.P., which had passed a 100 mesh screen, was added to the hot oil, with stirring. Stirring the slurry was considered to be important since the ferrous sulfate had a tendency to drop out of the oil as soon as the stirring was stopped.

The heated mixed slurry was spray cooled, at a rate of 700–750 lbs. per hour, using a spray pressure of 300–500 psi into a commercial spray tower with air at 30°–40° F. The resulting particulate material was a free-flowing granular material which substantially passed a 100 mesh screen.

The particulate material is applied to a breakfast cereal by sprinkling the particles on to the cereal as the flakes emerge from the toasting oven, while the flakes are still hot. The flakes are then permitted to cool and are then processed in the usual manner.

EXAMPLE 2

Using the procedure described above, 1698 pounds of the same distilled monoglycerides from hydrogenated cottonseed oil was heated and mixed with 638 pounds of dried ferrous sulfate U.S.P. The heated dispersion was spray cooled to produce a free-flowing granular material which contained about 27.3% by weight of ferrous sulfate.

EXAMPLE 3

The samples described below (except for an iron-free control sample) were prepared by adding the various iron compounds, in the quantities shown in Table 1, to a cereal-based breakfast food substrate. The food substrate used for all samples were portions of "Rice Krispies," made in the Kellogg Company Research Department according to the commercial process used by the Kellogg Company with only such modifications as were necessary to accommodate the specific test being made. The process for commercial production of "Rice Krispies" includes a cooking step, a drying step, a bumping step, another drying step, a tempering step and an oven puffing step, emerging from which the food typically has a surface temperature in excess of 160° F.

The samples designated below as "cooked in" were prepared by adding the indicated quantity of the iron compound to the rice prior to the cooking step and the samples were then completed, as indicated above.

The samples designated below as "fat encapsulated" were prepared by applying fat encapsulated ferrous sulfate to the "Rice Krispies" as they emerged from the puffing oven at a temperature of 425° F., at a rate sufficient to produce the indicated level of iron enrichment. The fat encapsulated iron was manufactured in the manner of Example 1 and contained 50% by weight of ferrous sulfate dispersed in distilled monoglycerides. The helping of cereal is assumed to be a one ounce portion. The actual iron loading, expressed in milligrams of iron, calculated as pure iron, per ounce of cereal as determined by analysis is reported in Table 1, followed by the target value for the iron loading, expressed in terms of RDA percentage.

Several portions of each sample were packaged in standard breakfast cereal cartons; a number of such portions of each sample were stored in a hot room maintained at a temperature of 100° F. and a relative humidity of 12–15%, and a second set of portions of each sample was stored under normal ambient conditions. A portion of each sample stored in the hot room was tested at one-week intervals, starting with the second week, and cartons of each sample stored under normal ambient conditions were tested at two-week intervals.

The samples were each tested by a panel of five employees of Kellogg Company believed to be reasonably skilled and expert in the analysis of cereal breakfast foods. Each member of the panel was required to score each sample, the scoring basis summarized as follows:

| Acceptable: | No defects or defects recognizable by an expert but not recognizable as such by consumers. |
|---|---|
| B.S.L.: | Below standard limitations. Defects noticable by consumers, e.g., off-taste. |
| Unsatisfactory: | Essentially inedible, e.g., rancid. |

The samples were all served to the members of the panels as oven-puffed rice breakfast cereals, in bowls with cold milk, and with sample identification not known to or recognizable or decipherable by the members of the panel. The results after eight weeks are shown below in Table 1:

TABLE 1

| Iron Compound | Mg of Fe per Oz of cereal | | Application Technique | Results At Room Temperature After 12 Weeks | Results At Hot Room After Stated Time (weeks) | |
|---|---|---|---|---|---|---|
| Reduced Iron | 3.6 | (25% RDA) | cooked in | A | A<br>B-Slightly off-odor and taste | 2–4<br>4–8 |
| Reduced Iron | 11.5 | (68% RDA) | Cooked in | B-gray color, slight metallic taste | U-rancid | 2 |
| FeSO$_4$ | 2.7 | (10% RDA) | Cooked in | B-off-gray color, off-metallic taste | A-gray color<br>B-off-dark color, off-odor & taste<br>U-off-dark color, off-bad odor and taste discontinued | 2<br>4–6<br>8 |
| FeSO$_4$ | 2.0 | (10% RDA) | Fat encapsulated | A | A<br>B-slightly off-odor | 2–6<br>8 |
| FeSO$_4$ | 4.6 | (25% RDA) | Cooked in | B-off-gray color, off-metallic taste | U-rancid | 2 |
| FeSO$_4$ | 2.2 | (25% RDA) | Fat encapsulated | A | A<br>B-slightly off-odor | 2–6<br>8 |
| FeSO$_4$ | 10.0 | (50% RDA) | Cooked in | B-dark, off-metallic taste | U-rancid | 2 |
| FeSO$_4$ | 6.4 | (50% RDA) | Fat encapsulated | A-slight off-taste | A<br>B-off-odor & taste<br>U-rancid | 4<br>6<br>8 |
| No Iron | 0 | | — | A | A | 2–6 |

TABLE 1-continued

| Iron Compound | Mg of Fe per Oz of cereal | Application Technique | Results At Room Temperature After 12 Weeks | Results At Hot Room After Stated Time (weeks) |
|---|---|---|---|---|
| | | | | B-slightly off-odor 8 |

A-means acceptable
B-means below standard limits
U-means unsatisfactory

All samples which contained "cooked in" ferrous sulfate were discolored. It has been found that one week of storage at 100° F. correlates well with one month of storage at ambient temperature with respect to rancidity. Therefore all of the "cooked in" samples were not satisfactory for commercial purposes with respect to shelf life.

EXAMPLE 4

Using the techniques of Example 3, the storage stability of iron enriched "Rice Krispies" was determined for different forms of iron enrichment. The results are reported below:

TABLE 2

| Iron Source | Mg of Fe per oz of cereal | Results after stated time | |
|---|---|---|---|
| FeSO$_4$ - Cooked in | 4.2 | HR — | 12 wk — A |
| | | RT — | 12 mo — A |
| | 3.6 | HR — | 13 wk — A |
| | | HR — | 15 wk — U |
| | | RT — | 9 mo — A |
| Reduced Iron Cooked in | 4.0 | HR — | 2 wk — A |
| | | RT — | 10 mo — U |
| | 2.8 | HR — | 12 wk — A |
| | | RT — | 10 mo — B |
| FeSO$_4$ - sprayed on | 6.8 | HR — | 2 wk — U |
| | | RT — | 1 mo — U |
| 25% FeSO$_4$ - in distilled monoglycerides | 4.9 | HR — | 12 wk — A |
| | | | 18 wk — B |
| | | RT — | 9 mo — A |
| | | | 12 wk — B |
| 25% FeSO$_4$ - in purified cottonseed oil | 3.6 | HR — | 20 wk — B |
| | | RT — | 6 mo — A |
| | | | 12 mo — B |
| | 4.7 | HR — | 20 wk — A |
| | | RT — | 7 mo — A |
| | | | 12 mo — B |
| 34% FeSO$_4$ - in distilled monoglycerides | 5.1 | HR — | 16 wk — A |
| | | RT — | 5 mo — A |
| | | | 12 mo — B |
| 34% FeSO$_4$ - in purified cottonseed oil | 6.4 | HR — | 10 wk — A |
| | | | 20 wk — B |
| | | RT — | 12 mo — B |
| | 4.8 | HR — | 20 wk — A |
| | | RT — | 20 wk — A |
| | | | 12 mo — B |
| 50% FeSO$_4$ - in distilled monoglycerides | 5.7 | HR — | 18 wk — A |
| | | RT — | 12 mo — A |
| 50% FeSO$_4$ - in purified cottonseed oil | 3.0 | HR — | 20 wk — B |
| | | RT — | 4 mo — A |
| | | | 12 mo — B |
| | 5.8 | HR — | 12 wk — A |
| | | | 16 wk — B |
| | | RT — | 12 mo — B |

Footnote:
HR means storage at 100° F.
RT means storage at ambient temperatures
A means acceptable
B means below standard limits
U means unacceptable.

The results of Examples 3 and 4 demonstrate that it is possible to use very low levels of reduced iron and to provide some iron enrichment of the food without producing excess taste and/or excessive loss of storage stability. However, when forms of iron which have a higher biological availability are employed, such as ferrous sulfate, the taste problem and the loss of storage stability are aggravated unless the iron is encapsulated in fat, in accordance with the present invention.

The tests also show that when operating near 10% of the RDA with ferrous sulfate that some loss of storage stability is encountered. Although no significant deterioration would be expected at 10% of the RDA using reduced iron, when reduced iron was used at a biological availability level equivalent to 10% of the RDA of ferrous sulfte (18 mg × 10% × 1/37% = 4.86 mg), rancidity rapidly appears. For commercial purposes it is deemed necessary to have at least a marginally acceptable product after 12 months storage at room temperature and/or 12 weeks at 100° F.

Flavor problems and loss of storage stability of the same type and kind, although not necessarily with identical magnitude, are encountered in reinforcing other types of breakfast cereals, such as cornflakes and the like. "Rice Krispies" were chosen for the tests of Examples 3 and 4 simply because previous experience had shown them to be very consistent and reproduceable in storge stability tests and flavor tests. Cornflakes, on the other hand, have shown erratic results, although the overall problem is of the same kind and similar magnitude to that displayed by "Rice Krispies."

EXAMPLE 5

Using the techniques described in Examples 1 and 2, six separate food supplements were made up using a distilled monoglyceride (minimum 90% monoester) having a melting point of 152°–168° F. The food supplements contained the following components:

1. Mixture of Vitamin A and Vitamin D.
2. Thiamine.
3. Riboflavin.
4. Pyridoxine.
5. Vitamin B$_{12}$.
6. Vitamin C.

Each of the six separate food supplements were combined by mixing. The product could be added to cereal flakes in the manner described in Example 1. The total product was analyzed to show 77% by weight of the monoglyceride fat. The vitamin potency of 74.9 milligrams of the product was as follows:

1333 U.S.P. Units Vitamin A Palmitate
133 U.S.P. Units Vitamin D$_2$
0.33 mg. Thiamine Hydrochloride
0.40 mg. Riboflavin
0.60 mg. Pyridoxine Hydrochloride
1.6 mcgm. Vitamin B$_{12}$
10.0 mg. Sodium Ascorbate.

EXAMPLE 6

Particles of fat-coated ferrous sulfate, as described in Example 1 were introduced into the manufacture of spaghetti at different levels to determine its effect on the quality of the product and its shelf life.

Spaghetti was manufactured on a pilot basis using the fat-coated ferrous sulfate as follows:

Sample A — Control 100% Semolina (unenriched)
Sample B — 20 mg of Fe per pound
Sample C — 25 mg of Fe per pound
Sample D — 30 mg of Fe per pound.

After an accelerated aging test which was deemed to be equivalent to about 10 months of ordinary storage, all of the samples had a normal appearance and Samples A and B had normal taste. Samples C and D had developed a slight metallic taste, but developed no rancidity. A cooking test showed that the cooked spaghetti product retained at least 97% of the original iron.

EXAMPLE 7

A food supplement containing 50% by weight of ferrous sulfate was made up in accordance with the teachings of Examples 1 and 2. The food supplement, which contained 14.5% Fe, was used in a pilot plant manufacture of spaghetti as follows:

Sample A - Control 100% Semolina
Sample B - 16.5 mg of Fe per pound
Sample C - 25 mg of Fe per pound.

The products were processed in a normal manner and produced good cohesive doughs with good color appeal. A sub-division of each of the above three products was placed in a stability oven at a temperature of 100° F. at a relative humidity of 50% in order to determine shelf life. The products were periodically withdrawn from this stability oven and subjected to organoleptic analysis by a panel of three in order to determine the keeping quality as evidenced by change in odor and taste. At the accelerated temperature of 100° F. the shelf life is evaluated as follows:

One week at 100° F. is equivalent to one month of storage at room temperature. This study was continued for a period of twelve weeks which, in our opinion, is equivalent to a normal storage period of twelve months.

Cooking Tests

The above three products were subjected to cooking tests at different intervals and the cooked spaghetti was evaluated by our panel with emphasis placed on appearance and taste.

Cooking tests were made on these products initially followed by cooking tests evaluation after four weeks, six weeks, eight weeks, nine weeks, ten weeks, eleven weeks and twelve weeks.

The results are outlined in the following table:

| | COOKING TEST STUDY | | |
| --- | --- | --- | --- |
| Product | Time—weeks | Taste | Appearance |
| Sample A | 4–11 weeks | Normal | Normal |
| Sample B | 4–11 weeks | Normal | Normal |
| Sample C | 4–11 weeks | Normal | Normal |
| Sample A | 12 weeks | Normal | Normal |
| Sample B | 12 weeks | Normal | Normal |
| Sample C | 12 weeks | Slightly Metallic | Normal |

Cooking Test Evaluation

The spaghetti at a level of 25 mg. of iron was subjected to our official cooking test in order to determine the retention of iron during the cooking process. The results are as follows:

| | Iron Fe Mg/lb. (Uncooked) | Iron Fe Mg/lb. (Cooked) | Iron Fe Retention of Iron % |
| --- | --- | --- | --- |
| Sample C | 28.7 | 27.9 | 97.2 |
| Sample C | 28.0 | 27.0 | 96.9 |

The results of two cooking tests show that the amount of iron retained in the cooked macaroni product averages 97% or better.

Although the examples set forth above describe the production of food supplements containing between about 20 to 30% by weight of iron compounds, vitamins, minerals or mixtures thereof, it will be obvious to those skilled in the art that greater or lesser quantities may be used. From about 25% to about 75% by weight of the food supplement is considered a useful range for the iron compounds in general, as well as for ferrous sulfate. It is generally desired that the quantity of the iron compound be kept sufficiently low that the edible fat can substantially completely coat the iron compound and thereby mask its flavor and color producing tendencies. The present invention contemplates the use of the same range for food supplements containing vitamins, minerals or mixtures thereof.

It has been found that conventional spray drying and cooling nozzles and towers may be used to prepare granular compositions which will pass a 80 mesh screen, as illustrated in the examples. Screen analysis of two runs made on such equipment is given below.

| U.S. Sieve Size | Run A | Run B |
| --- | --- | --- |
| +50 | 18.4 | 0.8 |
| +60 | 3.4 | 0.6 |
| +80 | 41.4 | 8.1 |
| +100 | 7.2 | 11.9 |
| −100 | 26.8 | 78.1 |

If finer sizes are desired the material may be cryogenically cooled and ground in a micropulverizer. Generally it is convenient to have the product between 10 and 300 mesh, with about 80 mesh being preferred.

As will be apparent to those skilled in the art a variety of different production means can be employed, although as is illustrated by the example above, the spray cooling tower provides a convenient mechanism for coating iron compounds, vitamins, minerals or mixtures thereof with the fat.

It will be obvious to those skilled in the art that the food supplement may contain various auxiliary materials in addition to the fat and iron-compounds, vitamins, minerals or mixtures thereof. For instance, one may add various preservatives or anti-oxidants to enhance the shelf life of the food supplement. Anti-caking materials such as silicon dioxide may be added to the edible fat. The present invention also contemplates the use of excepients which promote the release of iron compounds, vitamins, minerals or mixtures thereof in the digestive tract. Coloring materials such as vegetable dyes may likewise be employed. Additional modifying materials will be obvious to those skilled in the art.

The present invention provides a convenient way to enrich cereal-based breakfast foods, such as the breakfast foods toasted during their production. By applying the fat-coated food supplement to the flakes during, or shortly after the toasting process, the food supplement is firmly bound via the fat to the flake in a manner that it will not separate during subsequent packaging, handling, and storage. Under the conditions at which the cereal is generally stored, the fat will not deteriorate, but will give good shelf life. When the cereal is to be eaten and is mixed with milk, the fat will not dissolve, but will hold the food supplement in a form where the food supplement components will not flavor the cereal or impart an unnatural taste to the user.

The food supplement of the present invention may be applied to base foods by various means, including mechanical vibrators and shakers of various types. For instance, in the production of foods which are subjected to a toasting or heating process, such as the corn-based breakfast cereals sold under the trade name "Cornflakes," as the foods emerge from the oven in which they are toasted or heated, a vibrator-shaker arrangement above the belt can be used to sprinkle the fat-covered food supplement on to the flakes before they have cooled. The heat of the toasted foods melts a portion of the fat carrier which in turn holds the food supplement components to the food. When the base foods cool, the food supplement will be affixed thereto in the form of a nearly invisible layer of food supplement components in a taste-free edible fat carrier. Although not all of the fat-covered food supplement will adhere to the food, it is possible to recover that portion which does not adhere to the flakes, and recycle it for further use. Thus in the coating operation there is practically no waste of the food supplement. It will be obvious to those skilled in the art that many other shaking or dusting mechanisms for applying the food supplement to the base food may be used.

As was mentioned above, the daily dietary requirement (RDA) for iron is approximately 18 milligrams for an adult. It has been found possible to supplement foods with the present invention in order to provide up to 100% of a daily requirement per helping of cereal. This can be accomplished by adding 20 to 100 milligrams of the edible fat-coated iron compounds, described herein, to a portion of breakfast cereal.

In addition to the grain based breakfast cereals, this material may be used on crackers, cookies, potato chips, and similar snack foods, flour and pasta. Generally it has been found that the shelf life of the product so coated is good.

The forms of the invention herein shown and described are to be considered only as illustrative. It will be apparent to those skilled in the art that numerus modifications may be made therein without departure from the spirit of the invention or the scope of the appended claims.

We claim:

1. A process for producing a base food product with a food supplement on at least a portion of the surface thereof, said food supplement comprising finely divided particles of an edible, metabolizable fat carrier having a melting point between about 100° and 250° F., said fat carrier having admixed therein a nutrient selected from the group consisting of an assimilable iron compound, vitamins, minerals, and mixtures thereof;

said process comprising:

Processing a base food product at a temperature above said melting point of said fat carrier;

applying said food supplement to at least a portion of the surface of said face food product while said surface is at a temperature above said melting point;

maintaining said food supplement in contact with said base food product for a time sufficient to permit at least a portion of said food supplement fat carrier to melt and adhere to the surface of said base food product; and, cooling said food product to a temperature below the melting point of said fat.

2. A process for producing a base food product with an iron-containing food supplement on at least a portion of the surface thereof, said food supplement comprising finely divided particles of an edible, metabolizable fat carrier having a melting point between about 100° and 250° F., said fat carrier having admixed therein an assimilable iron compound;

said process comprising:

processing a base food product at a temperature above said melting point of said fat carrier;

applying said food supplement to at least a portion of the surface of said base food product while said surface is at a temperature above said melting point;

maintaining said food supplement in contact with said base food product for a time sufficient to permit at least a portion of said food supplement fat carrier to melt and adhere to the surface of said base food product; and, cooling said food product to a temperature below the melting point of said fat.

3. A process for producing a base food product with a food supplement on at least a portion of the surface thereof, said food supplement comprising finely divided particles of an edible, metabolizable fat carrier having a melting point between about 100° and 250° F., said fat carrier having admixed therein a nutrient selected from the group consisting of vitamins and minerals;

said process comprising:

processing a base food product at a temperature above said melting point of said fat carrier;

applying said food supplement to at least a portion of the surface of said base food product while said surface is at a temperature above said melting point;

maintaining said food supplement in contact with said base food product for a time sufficient to permit at least a portion of said food supplement fat carrier to melt and adhere to the surface of said base food product; and, cooling said food product to a temperature below the melting point of said fat.

4. A process for producing a base food product with a vitamin containing food supplement on at least a portion of the surface thereof, said food supplement comprising finely divided particles of an edible, metabolizable fat carrier having a melting point between about 100° and 250° F., said fat carrier having at least one vitamin admixed therein;

said process comprising:

processing a base food product at a temperature above said melting point of said fat carrier;

applying said food supplement to at least a portion of the surface of said base food product while said surface is at a temperature above said melting point;

maintaining said food supplement in contact with said base food product for a time sufficient to permit at least a portion of said food supplement fat carrier to melt and adhere to the surface of said base food product; and, cooling said food product to a temperature below the melting point of said fat.

5. A process for producing a base food product with a mineral containing food supplement on at least a portion of the surface thereof, said food supplement comprising finely divided particles of an edible, metabolizable fat carrier having a melting point between about 100° and 250° F., said fat carrier having a mineral admixed therein;

said process comprising:

processing a base food product at a temperature above said melting point of said fat carrier;

applying said food supplement to at least a portion of the surface of said base food product while said surface is at a temperature above said melting point;

maintaining said food supplement in contact with said base food product for a time sufficient to permit at least a portion of said food supplement fat carrier to melt and adhere to the surface of said base food product; and, cooling said food product to a temperature below the melting point of said fat.

6. A process for preparing a toasted cereal-based flaked food product, with a food supplement on at least a portion of the surface thereof, said food supplement comprising finely divided particles of an edible, metabolizable fat carrier having a melting point between about 100° and 250° F., said fat carrier having admixed therein a nutrient selected from the group consisting of an assimilable iron compound, vitamins, minerals, and mixtures thereof;

said process comprising:

toast processing said flaked food product;

applying said food supplement to at least a portion of said flake surfaces while said surface is at a temperature above the melting point of said fat carrier;

maintaining said food supplement in contact with said flake surfaces for a time sufficient to permit at least a portion of said food supplement fat carrier to melt and adhere to said flake surfaces; and, cooling said flaked product to a temperature below the melting point of said fat.

7. A process for preparing a toasted cereal-based flaked food product, with an iron-containing food supplement on at least a portion of the surface thereof, said food supplement comprising finely divided particles of an edible, metabolizable fat carrier having a melting point between about 100° and 250° F., said fat carrier having admixed therein an assimilable iron compound;

said process comprising:

toast processing said flaked food product;

applying said food supplement to at least a portion of said flake surfaces while said surface is at a temperature above the melting point of said fat carrier;

maintaining said food supplement in contact with said flake surfaces for a time sufficient to permit at least a portion of said food supplement fat carrier to melt and adhere to said flake surfaces; and, cooling said flaked product to a temperature below the melting point of said fat.

8. A process for preparing a toasted cereal-based flaked food product, with a food supplement on at least a portion of the surface thereof, said food supplement comprising finely divided particles of an edible, metabolizable fat carrier having a melting point between about 100° and 250° F., said fat carrier having admixed therein a nutrient selected from the group consisting of vitamins and minerals;

said process comprising:

toast processing said flaked food product;

applying said food supplement to at least a portion of said flake surfaces while said surface is at a temperature above the melting point of said fat carrier;

maintaining said food supplement in contact with said flake surfaces for a time sufficient to permit at least a portion of said food supplement fat carrier to melt and adhere to said flake surfaces; and, cooling said flaked product to a temperature below the melting point of said fat.

9. A food product comprising a base food having a food supplement affixed to at least a portion of the surface of said base food, said food supplement comprising finely divided particles of an edible, metabolizable fat carrier having mixed therein a nutrient selected from the group consisting of an assimilable iron compound, vitamins, minerals, and mixtures thereof, said fat carrier having a melting point between about 100° and 250° F., said fat carrier serving to affix said food supplement to said base food, said food supplement being present in sufficient quantity to comprise at least 10% of the RDA of the nutrient, per serving of said base food.

10. A food product comprising a base food having food supplement affixed to at least a portion of the surface of said base food, said food supplement comprising finely divided particles of an edible, metabolizable fat carrier having admixed therein an assimilable iron compound, said fat carrier having a melting point between 100° and 250° F., said fat carrier serving to affix said food supplement to said base food, said food supplement being affixed to said base food in sufficient quantity to provide an assimilable iron compound containing at least 1.8 mg of iron (calculated as pure iron) per ounce of said base food.

11. A food product as described in claim 10, wherein said assimilable iron compound comprises ferrous sulfate.

12. A food product as desribed in claim 11, wherein said base food is breakfast cereal.

13. A food product comprising a base food having a food supplement affixed to at least a portion of the surface of the said base food, said food supplement comprising finely divided particles of an edible, metabolizable fat carrier having admixed therein an assimilable iron compound, said food supplement containing from about 25 to about 75% by weight of said fat carrier and from about 25 to about 75% by weight of said assimilable iron compound, said fat carrier having a melting point between about 100° and 250° F., said fat carrier serving to affix said food supplement to said base food, said base food having affixed thereto from about 20 to about 100 mg of said food supplement per ounce of said base food.

14. A food product as described in claim 13, wherein said assimilable iron compound is ferrous sulfate.

15. A food product as described in claim 13, wherein said base food is a breakfast cereal.

\* \* \* \* \*

UNITED STATES PATENT AND TRADEMARK OFFICE
CERTIFICATE OF CORRECTION

PATENT NO. : 3,992,556
DATED : November 16, 1976
INVENTOR(S) : Kovacs et al.

It is certified that error appears in the above–identified patent and that said Letters Patent are hereby corrected as shown below:

Column 4, line 2; "thse" should be --these--; Column 8, line 4, "425°E" should be --425°F--; Column 8, line 43, "identification" should be --identifications--; Column 14, line 2, "face" should be --base--; Column 14, line 16 (Claim 1), "metalbolizable" should be --metabolizable--.

Signed and Sealed this

Eighth Day of March 1977

[SEAL]

Attest:

RUTH C. MASON
Attesting Officer

C. MARSHALL DANN
Commissioner of Patents and Trademarks